(12) United States Patent
Woods

(10) Patent No.: US 7,874,243 B2
(45) Date of Patent: Jan. 25, 2011

(54) BEVERAGE FRESHNESS MONITORING SYSTEM AND METHOD

(76) Inventor: Charles A. Woods, 505 Iroquois Shore Road, Unit 6, Oakville, ON (CA) L6H 2R3

(*) Notice: Subject to any disclaimer, the term of this patent is extended or adjusted under 35 U.S.C. 154(b) by 874 days.

(21) Appl. No.: 11/734,440

(22) Filed: Apr. 12, 2007

(65) Prior Publication Data

US 2008/0254173 A1 Oct. 16, 2008

(51) Int. Cl.
*A47J 31/00* (2006.01)
*G01K 1/08* (2006.01)
*G01K 1/14* (2006.01)

(52) U.S. Cl. .......................... 99/285; 99/323.3; 374/102; 374/141

(58) Field of Classification Search ................. 99/285, 99/323.3, 280, 281, 282, 283; 368/10, 101, 368/108, 121; 340/309.16, 588, 691.6, 309.4; 374/102, 141, 142, 150, 104, 106
See application file for complete search history.

(56) References Cited

U.S. PATENT DOCUMENTS

| | | | |
|---|---|---|---|
| 4,566,802 A | 1/1986 | Koehler | |
| 4,671,668 A | 6/1987 | Narita et al. | |
| 4,838,152 A | 6/1989 | Kubicko et al. | |
| 5,001,969 A | 3/1991 | Moore et al. | |
| 5,094,153 A * | 3/1992 | Helbling | ...................... 99/280 |
| 5,129,352 A | 7/1992 | Roberts | |
| 5,239,519 A | 8/1993 | Nelson et al. | |
| 5,260,914 A | 11/1993 | Roberts | |
| 5,684,759 A | 11/1997 | Huang et al. | |
| 5,854,774 A * | 12/1998 | Timme | ......................... 368/10 |
| 5,923,257 A * | 7/1999 | Nolte | .......................... 340/584 |
| 6,564,696 B2 | 5/2003 | Koncelik, Jr. | |
| 6,588,593 B2 | 7/2003 | Woskoski | |
| 7,096,776 B2 | 8/2006 | Koncelik, Jr. | |
| 7,637,204 B2 * | 12/2009 | Sumser et al. | ................. 99/279 |
| 2005/0083182 A1 * | 4/2005 | Contadini | .............. 340/309.16 |
| 2005/0105395 A1 | 5/2005 | Harrison | |
| 2005/0188856 A1 | 9/2005 | Sumser et al. | |
| 2005/0207282 A1 | 9/2005 | Kwan et al. | |
| 2006/0283329 A1 | 12/2006 | Ronci | |

FOREIGN PATENT DOCUMENTS

JP 55-151287 * 11/1980

* cited by examiner

*Primary Examiner*—Reginald L Alexander
(74) *Attorney, Agent, or Firm*—Bereskin & Parr LLP/S.R.N.C.R.L.,s.r.l.; Philip C. Mendes da Costa

(57) ABSTRACT

A timer system for monitoring the freshness of a beverage in a plurality of carafes, and a method of use are disclosed. The timer system comprises a plurality of matched pairs of timers and signaling members, with each timer being individually actuateable and each signaling member being drivingly controlled by its matched timer to issue a signal after the matched timer has operated for a preset period of time. A housing mountable on a beverage preparation device houses the timers. A plurality of tags are mounted to a plurality of carafes to create a plurality of matched carafes that correspond to the plurality of matched pairs of timers and signaling members. After the beverage in a matched carafe is prepared, the matched timer is activated. After the timer has operated for a preset period of time, the matched signaling member then issues a signal, permitting the monitoring of the freshness of the beverage in the matched carafe.

18 Claims, 4 Drawing Sheets

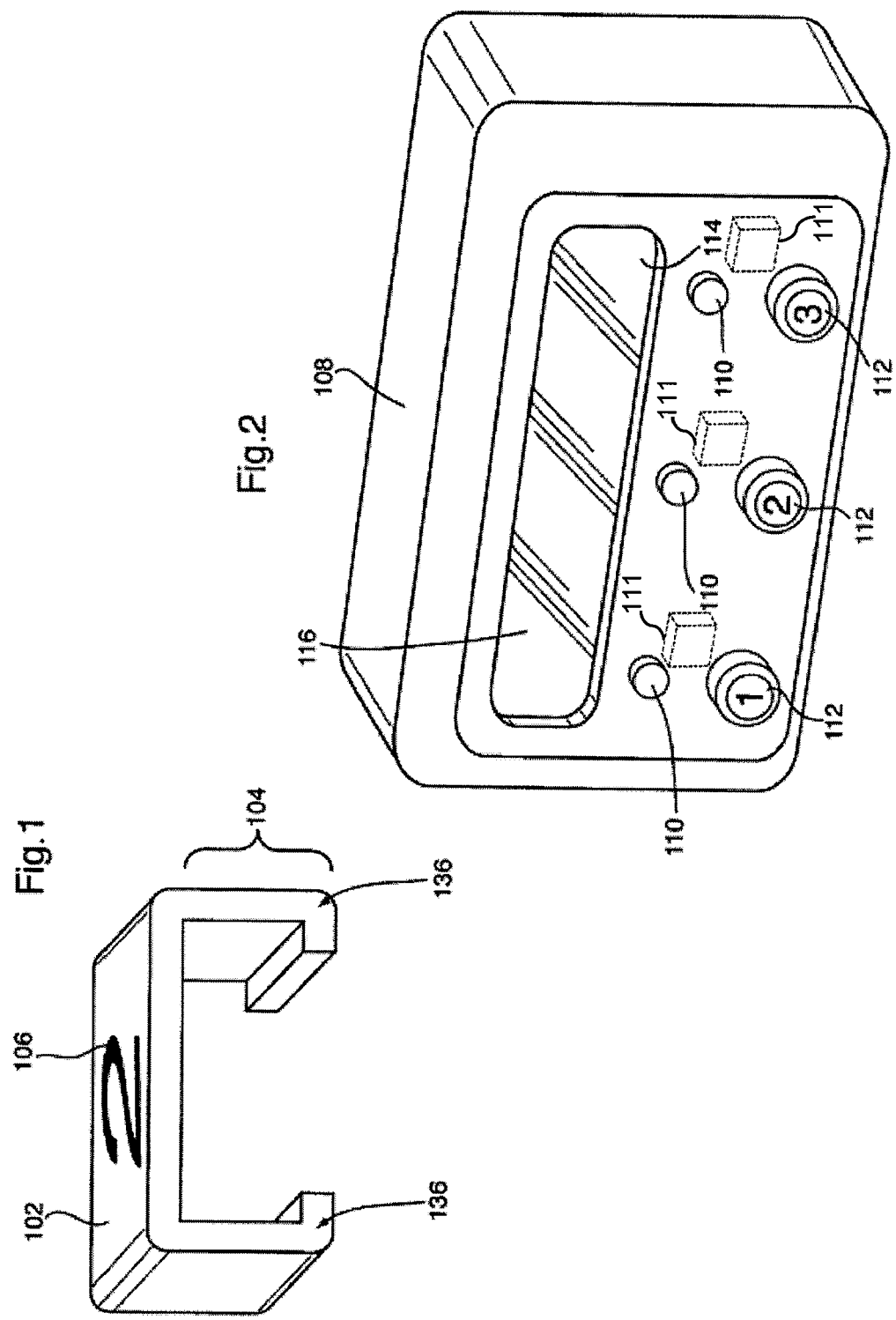

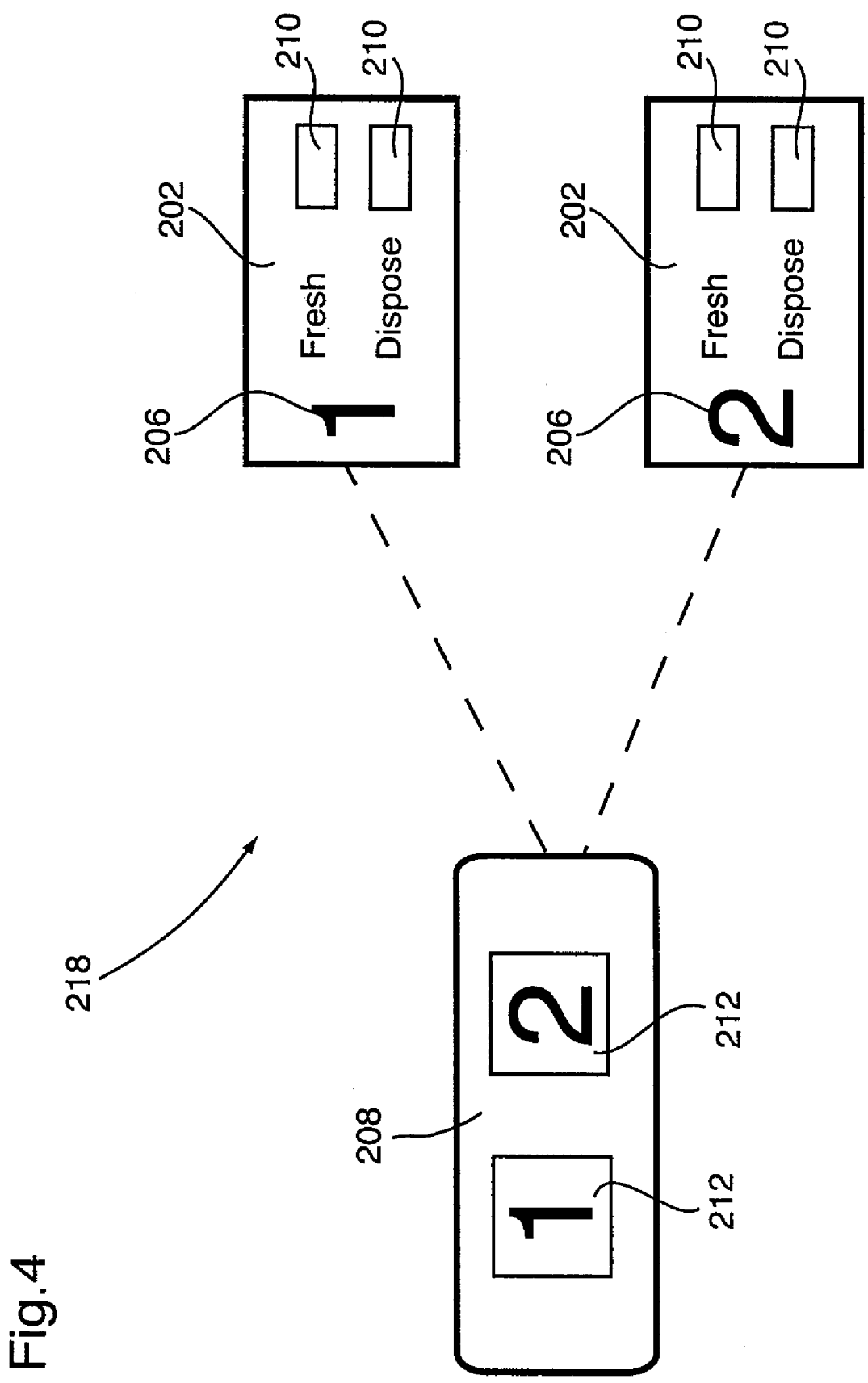

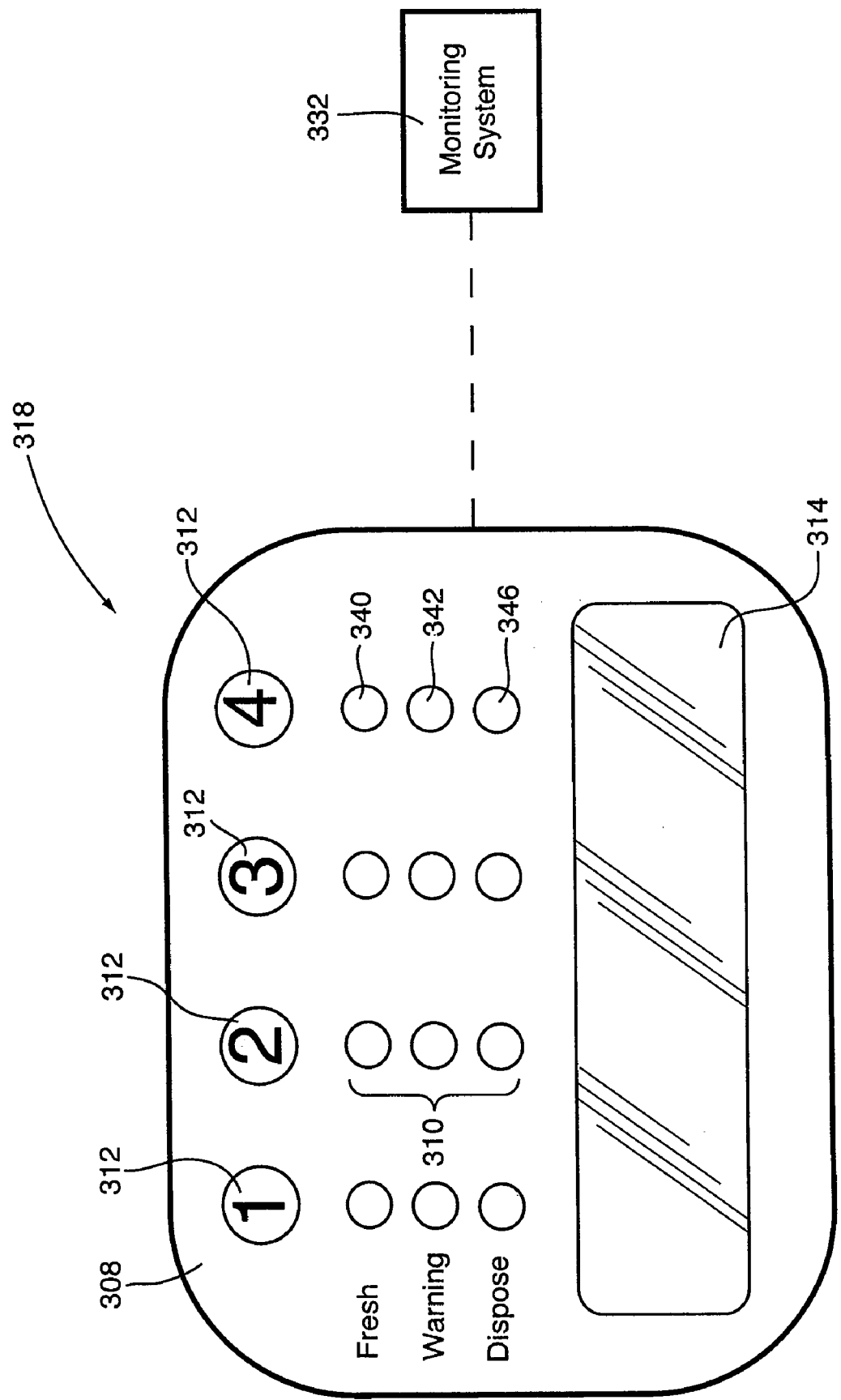

BEVERAGE FRESHNESS MONITORING SYSTEM AND METHOD

FIELD OF THE INVENTION

In one aspect, this invention relates to a system for monitoring beverage freshness, and in particular a timer system for monitoring the freshness of a beverage in a plurality of carafes. In accordance with another aspect, this invention relates to a system and method to monitor the operating of a beverage preparation device, such as an apparatus to brew coffee. For example, the usage of the beverage preparation device is monitored. Alternately, or in addition, the performance of the beverage preparation device is monitored to determine when service may be required.

BACKGROUND OF THE INVENTION

It is important for commercial establishments that sell beverages, for example hot tea, coffee, hot chocolate, iced tea, beer or any other type of beverage, that the beverage being served to a customer is fresh. This helps ensure that the beverage is of sufficient quality and taste to please the consuming customer, so that the customer will return to that commercial establishment to purchase a beverage again. Some commercial establishments place specific time requirements on how long a beverage can sit after initial preparation and still be considered fresh. In some commercial establishments, once a beverage is no longer considered fresh, it is disposed of, and a fresh batch of the beverage is prepared.

It can be difficult for these commercial establishments to monitor the length of time that has passed since the initial preparation of the beverage. A particular example is coffee. Once brewed, coffee is typically stored in open topped carafes, which are placed on a hot plate to maintain the coffee at an acceptable temperature. Over time, coffee will become stale and its taste will change.

One example method to monitor the time since initial preparation is to have a user, such as an employee, note the time indicated on a clock when the initial preparation is completed. The user could, for example write the time down on a specified piece of paper, or simply mentally remember the noted time. Problems with this technique include the user forgetting to note the time of initial preparation of the beverage, or if a plurality of carafes is used to store the beverage, forgetting what noted time is applicable to what carafe.

Other techniques include placing a timing device, for example a stopwatch, on a carafe, or a plurality of carafes containing a beverage to be monitored for freshness. Problems with this technique include the timing device falling off the carafe, being damaged when the carafe is used to serve the beverage, or mixing up which timing device is matched with which carafe.

It can be difficult for the franchiser or the management of a company to monitor that the operator of a store is respecting the beverage freshness standards set out by the franchiser or the company. This can lead to the franchiser or company having difficulty maintaining uniform quality standards for freshness of beverages in its commercial establishments. Maintaining uniform standards of freshness for a beverage can be integral to the commercial success of a business.

SUMMARY OF THE INVENTION

In accordance with one aspect of this invention, a timing apparatus is provided which is capable of tracking several times at once, e.g., it may have several timers. Accordingly, for example, when each pot of coffee is prepared, a timer is actuated to commence tracking the age of the beverage. The brewed beverage is placed in a container, e.g., a carafe, and the carafe is tagged, e.g., by a colour coded band or the like applied to the carafe, to associate the carafe with the timer that has just been commenced, e.g., the timer may have a colour band that is the same as the colour band placed on the carafe. The timing apparatus will signal when the beverage should be disposed of. As the timing apparatus is capable of tracking several times concurrently, the timing apparatus may monitor the status of a brewed beverage in several containers and signal when the beverage in a particular container should be disposed of.

An advantage of this design is that a single apparatus is provided which contains several timers. Therefore, instead of constructing several individual units, each of which contains a timer, that are applied to different carafes, all of the electronics, and a single power source, may be provided in a single housing. This housing may be placed on the beverage preparation device, e.g. an apparatus to brew coffee or a wall nearby. Thus, the apparatus is less likely to be damaged by spills or by being dropped. Further, the device may be mounted in a position wherein it is readily viewable by customers. Therefore, customers may be assured that the beverage that they are served is fresh. Further, if a franchiser or company sends a quality assurance officer to the store, the quality assurance officer may surreptitiously check that the store complies with freshness guidelines set by the franchisor or store.

In accordance with this aspect of the invention, there is provided a timer system for monitoring the freshness of a beverage in a plurality of carafes, the timer system comprising:

(a) a plurality of matched pairs of timers and signaling members, each timer being individually actuateable and each signaling member being drivingly controlled by its matched timer to issue a signal after the matched timer has operated for a preset period of time;

(b) a housing mountable on a beverage preparation device and including the timers; and, (c) a plurality of tags mountable on a carafe, each tag once mounted on a carafe producing a matched carafe corresponding to a matched pair of timer and signaling member.

In one embodiment, the signaling member issues an end of life signal after the matched timer has operated for a preset period of time indicative that the beverage in the matched carafe is not fresh.

In another embodiment, the signaling member issues a warning signal after the matched timer has operated for a period of time indicative that the beverage in the matched carafe will be fresh for a only an additional preset period of time.

In another embodiment, the signaling member issues a signal indicative that the beverage in the matched carafe is fresh.

The timer system of claim 1 wherein the beverage is a brewed beverage.

In another embodiment, the timer system further comprises a monitoring system that records selected details of the actuations of the timer system.

In accordance with this aspect of the invention, there is also provided a method of monitoring the freshness of a beverage contained in a plurality of carafes, the method comprising the steps of:

(a) providing a beverage preparation device, a plurality of matched pairs of timers and a signaling members, the plurality of carafes and a plurality of tags, each tag corresponding to a matched pair of a timer and a signaling member and being mountable on a carafe;

(b) after preparing the beverage in a carafe, activating a timer corresponding to a tag on the carafe;

(c) monitoring the freshness of beverage in the carafe by monitoring the signaling member matched to the timer.

In one embodiment, the method further comprises positioning the matched pairs of timers and signaling members proximate the beverage preparation device.

In another embodiment, the method further comprises positioning the matched pairs of timers and signaling members on the beverage preparation device.

In another embodiment, the signaling member issues an end of life signal after the matched timer has operated for a preset period of time indicative that the beverage in the matched carafe is not fresh and the method further comprises disposing of the beverage in the carafe after the end of life signal is issued.

In another embodiment, the signaling member issues a warning signal after the matched timer has operated for a period of time indicative that the beverage in the matched carafe will be fresh for only an additional preset period of time and attempting to serve the beverage in the carafe before the end of life signal is issued.

In another embodiment, each tag includes a signaling member that is wirelessly actuateable by its matched timer and the method further comprises monitoring the freshness of the beverage in the carafe by also monitoring the signaling member of the tag.

In accordance with another aspect of this invention, the timing apparatus may store information on the number of actuations of timing cycles. For example, how many times a timer was started (i.e., how many pots of coffee were brewed) and the time when the timer was initiated each cycle (i.e., to provide data indicating when the store was busy and when there were fewer customers). This information is preferably transferable to a computer (such as by being transferred by a flash drive or transmitted over a wireless network). This data may be used by the store to adjust staffing levels and/or the number of containers of coffee that are available at different times during a day.

In accordance with this aspect of the invention, there is provided a method of monitoring a beverage preparation device using a timer system comprising a plurality of matched pairs of timers and signaling members corresponding to a plurality of carafes, each timer being individually actuateable, and a housing mountable on a beverage preparation device and including the timers, the method comprising:

(a) recording information relating to actuations of the timers; and, (b) downloading at least some of the information to a computer.

In one embodiment, information is wirelessly transmitted to a computer.

In another embodiment, the method further comprises brewing the beverage.

In another embodiment the beverage is coffee and the method further comprises brewing the coffee.

In accordance with another aspect of this invention, the timing apparatus may be used to track the performance of the beverage preparation device. For example, the beverage preparation device may be a coffee brewing machine. The machine will operate at a particular rate when new (e.g., it may brew a pot of coffee in 3 minutes). If the machine takes too long, this may indicate that service is required (e.g., a water conduit may be partially blocked). For example, a timer of the timing apparatus may be actuated when the machine is started. The timing apparatus may signal when the coffee should be brewed (e.g., a light may flash 3 minutes after the timing apparatus is actuated). If the machine is still brewing coffee when the light starts to flash, then service may be required.

In accordance with this aspect of the invention, there is provided a method of monitoring a beverage preparation device using a timer system comprising a plurality of matched pairs of timers and signaling members corresponding to a plurality of carafes, each timer being individually actuateable, and a housing mountable on a beverage preparation device and including the timers, the method comprising:

(a) concurrently actuating a timer and a beverage preparation cycle of the beverage preparation device, the beverage preparation having a predetermined cycle time;

(b) issuing a signal after the timer has operated for a preset period of time corresponding to the predetermined beverage preparation cycle.

In one embodiment, the method further comprises monitoring whether the beverage preparation device has completed the beverage preparation cycle when the signaling member issues a signal It will be appreciated that each of these aspects may be used individual or combined in a single timing system or utilized in any particular sub combination.

BRIEF DESCRIPTION OF THE DRAWINGS

For a better understanding of the present invention, and to show more clearly how it may be carried into effect, reference will now be made by way of example, to the accompanying drawings that show some embodiments of the present invention.

FIG. 1 is a perspective view of an a tag in accordance with an embodiment of this invention;

FIG. 2 is a perspective view of a timing apparatus in accordance with one embodiment of this invention that is for use with the tag of FIG. 1;

FIG. 4 is a drawing of a timing apparatus and an associated tag for a timer system in accordance with another embodiment of this invention; and, FIG. 5 is a drawing of a timing apparatus for a timer system in accordance with another embodiment of this invention.

Figure 3:
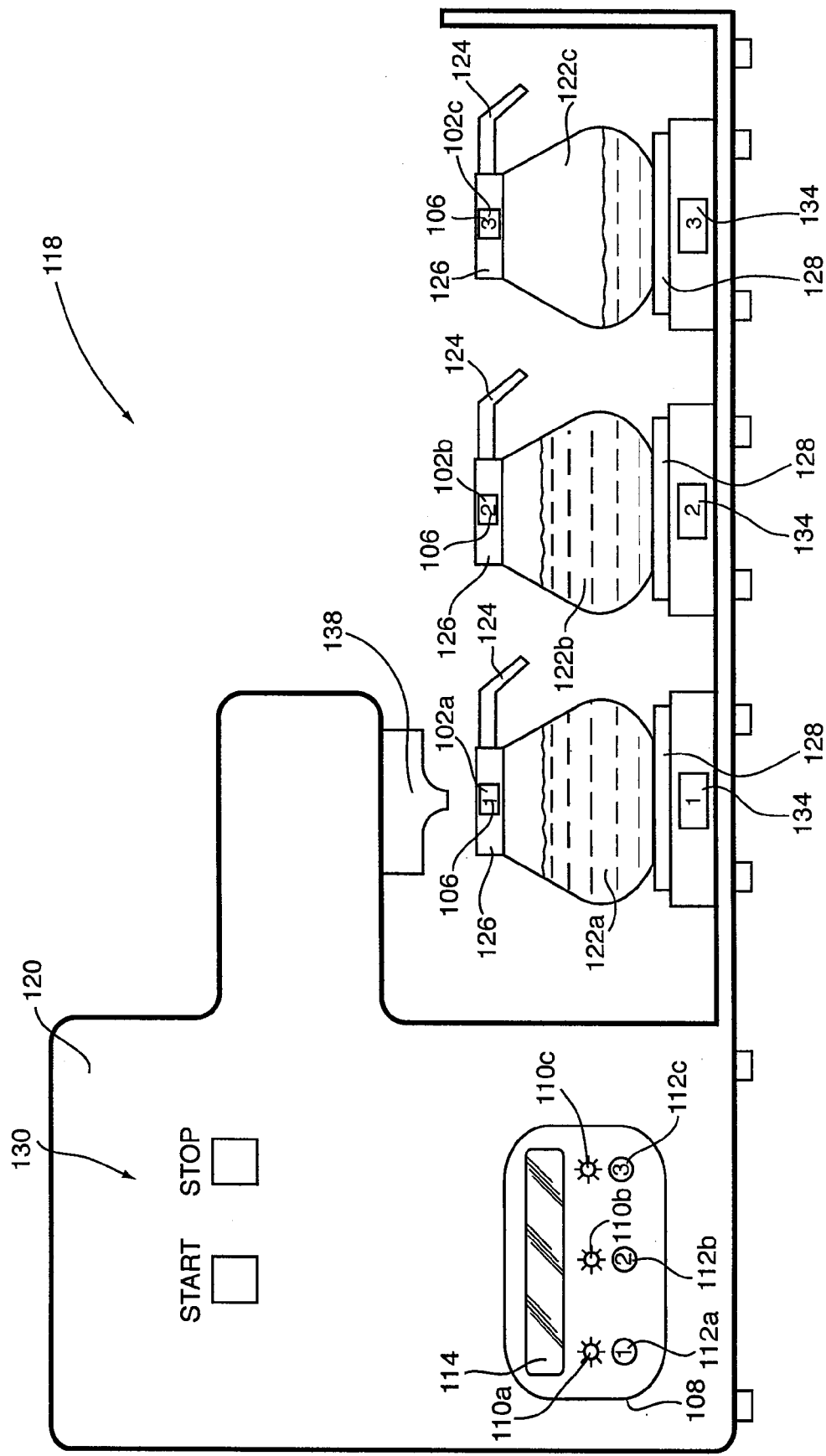
FIG. 3 is a timer system for monitoring the freshness of a beverage in a plurality of carafes, mounted on a beverage preparation device in accordance with an embodiment of this invention.

For simplicity and clarity of illustration, elements shown in the figures have not necessarily been drawn to scale. Further, where considered appropriate, reference numerals may be repeated among the figures to indicate corresponding or analogous elements.

DETAILED DESCRIPTION OF THE INVENTION

The beverage preparation device 120 is used to prepare any sort of beverage that may be sold by a commercial establishment. For example, the beverage preparation device 120 may prepare a brewed beverage, such as hot tea or coffee. In other embodiments the beverage preparation device 120 may prepare beverages such as hot chocolate, fruit juice, iced tea, filtered water, beer or any other type of beverage. Preferably, the beverage preparation device is used to brew coffee. Accordingly, the preferred embodiments exemplified herein are described with reference to a coffee brewing apparatus. However, it will be appreciated that the timing system may be used with other devices.

Reference is first made to FIGS. 1, 2 and 3 which shows an example of a timing system according to one aspect of the invention. The timing system 118 comprises a tag 102 and an associated housing 108 that includes a plurality of timers 111 provided within housing 108. Housing 108 may be mounted on beverage preparation device 120 (such as by being built into is or mounted on the exterior by, e.g., an adhesive or Velcro™) or be positioned nearby beverage preparation device 120. The tag 102 is provided on a carafe 122.

The carafes 122 are typically used to temporarily store and distribute the beverage prepared by the beverage preparation device 120. The carafes 122 may be any size or shape and any of those known in the art, or developed hereinafter, may be used. For example, the carafes 122 may be coffee carafes made of clear glass, with a handle 124 and collar 126, where the collar 126 may also comprises a pour spout for pouring the beverage stored in the carafe 122. In other embodiments, the carafe 122 may be a ceramic teapot or a closed toped stainless steel beverage container. The carafes 122 may have thermal insulation, or the carafes 122 may be maintained at a specified temperature via a heating or cooling element 128, e.g., a hot plate, which may be part of the beverage preparation device 120 or a separate apparatus. In other embodiments, any combination of different types of carafes may be used simultaneously on the same beverage preparation device 120 or a plurality of beverage preparation devices 120.

Tag 102 comprises one or more mounts 104 that permit the tag 102 to be mounted to a carafe 122. The tag 102 also comprises an identifying member 106 that associates the tag 102 to a corresponding matched pair of timer 111 and signaling member 110 provided on housing 108 so that when signaling member 110 issues a signal, a user will be able to identify the carafe to which the signal relates.

In some embodiments, the mount 104 may permanently mount the tag 102 to the carafe 122. In other embodiments the mount 104 may make the tag 102 removably mountable to the carafe 122. Preferably tag 102 is removably mounted to carafe 122. It will be appreciated that mount 104 may vary depending upon the carafe 122 that is used. The tags 102 may be mounted anywhere on the carafes 122, for example on the collar 126, on the handle 124, or elsewhere on the body of the carafe 122. Preferably, tag 102 is mounted on the carafe 122 in a location that is readily visible to a user.

For example, the mount 104 may be C-shaped brackets 136 for permitting mechanical interlock (or mating) between the tag 102 and the carafe 122. For example, C-shaped mounts may snap on to handle 124 of carafe 122 adjacent collar 126. In other embodiments, the mount 104 may be a system of hook and loop fasteners (e.g., Velcro™ fasteners), double-sided tape, mechanical interlock using means such as a screw or nut and bolt, application of an adhesive such as glue, or any other means of fastening the tag 102 to the carafe 122.

The identifying member 106 may be any sort of means for matching or associating a tag 102 to a corresponding matched pair of timer 111 and signaling member 110. For example, an identify marker may be applied to both the tag and one or both of the corresponding matched pair of timer 111 and signaling member 110. In some embodiments, the identifying member 106 may be one or more of a number, a shape (for example, a diamond, star or hexagon or any other type of shape), a colour (applied to part or all of a tag 102), or a letter.

As exemplified in FIG. 2, housing 108 comprises a plurality of timers 111 (which may be a circuit positioned inside housing 108), a plurality of signaling members 110, a plurality of start buttons 112, and mounting means (not shown). In some embodiments, the housing 108 may also comprise a solar panel 114. Alternately, or in addition, the housing 108 may comprise a display panel 116.

In some embodiments, the housing 108 includes a plurality of timers 111. For example the timers 111 may be located within the housing 108. The timer 111 may be an electro-mechanical timer, a timing circuit, or any other sort of device or system that can track time. In other embodiments, the timer 111 may be located remotely, for example in a computer, and may be remotely operably linked to the signaling members 110 located in the housing 108, such as by a wireless interface. The timer 111 may include a readout of the elapsed time since the timer was actuated and/or the time remaining until the beverage should be disposed of. The readout may be digital and may be provided on display 116 immediately above a respective button 112 and signaling member 110.

Each timer 111 drivingly controls the matched signaling member 110. The signaling member 110 may be an auditory signal or a visual signal. If the signaling member is a visual signaling member, then the signaling member may be one or more of an LED, an LCD, a light bulb, or any other type of illuminating device that can signal a user. Accordingly, the signaling member may be a separate light 110 or it may be provided as part of display panel 116. For example, a text message may be issued on the display panel 116 to signal a user. The signaling member 110 may emit a light of any color, some examples being green, yellow or red. The signaling member 110 may be capable of flashing or blinking. Accordingly, when signaling member is initiated, the user will be advised that the beverage should be disposed of. While the signaling member 110 may be provided on tag 102 (e.g., it is an auditory signal), it is preferred to be positioned as part of housing 108.

In an alternate embodiment, the signaling member 110 may be capable of changing color, for example from green to yellow to red. In some embodiments, the signaling member 110 may also be able to flash at a changing rate, for example progressively faster or slower, as the matched timer 111 nears having operated for a preset period of time. Accordingly, the signaling member may be a first colour when the beverage is just prepared (e.g., green and/or may provide a solid light). As the beverage ages, a warning may be provided that the beverage is approaching a point in time wherein it should be disposed of. For example, after a preset period of time, the signaling member may change colour (e.g., green to amber) and/or start flashing or start flashing faster and/or a differently coloured signaling member may be illuminated (e.g., if signaling member 110 comprises a plurality of LEDs). Alternately, or in addition, when the beverage has aged to a point wherein it should be disposed of, a disposal signal may be issued. For example, the signaling member may change colour (e.g., amber to red) and/or start flashing or start flashing faster and/or a differently coloured signaling member may be illuminated.

The start button 112 may be a button, a switch, a touch pad, a keystroke input, or any other means that can actuate (activate) a timer 111. If housing 108 is built into beverage preparation device 120, then a timer 111 may be actuated when the preparation (e.g., brewing cycle) is actuated. Accordingly, the start button of the device may be the start button for the timer 111. In some embodiments, the start button 112 may have an identifier visible to a user, for example, the start button 112 may have a number, a color, a letter, or a shape, that indicate to a user which matched timer 111, matched signaling member 110, and matched tag 102 correspond to that particular start button 112. As exemplified in FIG. 2, each start button 112 has an identifier and is positioned below its associated signaling member 110. It will be appreciated that the identifier may be provided on housing 108 in such a position to be associated with the correct button 112 and signaling member 110 by a user (e.g. above or below button 112 and signaling member 110).

The mounting means of the housing 108 may be a mechanical mating device, such as a nut and bolt, or a screw. Alternatively, it may be a hook and loop system (e.g. Velcro™ fastener), an adhesive, double-sided tape, or any other means of securing the housing 108 to a beverage preparation device 120. The housing 108 may be permanently mounted on the beverage preparation device 120, or the housing 108 may be removably mountable on the beverage preparation device 120.

Referring to FIG. 3, timer system 118 comprises a plurality of matched pairs of timers 111 (provided inside housing 108, shown in FIG. 2) and signaling members 110, and a plurality of tags 102. Housing 108 is preferably mounted on the beverage preparation device 120, preferably in a position where it is readily visible to a user and, more preferably, also visible to customers. For example, the housing 108 may be mounted adjacent to the controls of the beverage preparation device 120, or the housing 108 may be mounted adjacent to the docking stations of the plurality of carafes 122 on the beverage preparation device 120. The housing 108 may, in other embodiments, be simply located proximate to the beverage preparation device. For example, the housing 108 may be placed on a counter top (not shown) located adjacent to the beverage preparation device, or the housing 108 may be located on a wall or a cupboard, proximate the beverage preparation device 120, or the housing may be located next to a check out point (for example near the till) at a commercial establishment.

In addition, a docking station tag 134 may be mounted alone, or in duplicate to the tag 102 mounted on the carafe 122, on a docking station (e.g., hot plate) associated with the carafe 122. Placement of a docking station tag 134 on a carafe 122 docking station may assist a user in placing the carafe 122 on the correct docking station of the beverage preparation device 120. Docking station tag 134 may be used as a back up in case tag 102 is separated from its carafe 122.

In the embodiment shown in FIG. 3, three signaling members 110a, 110b, 110c are individually matched to three timers 111 (shown in FIG. 2), and to three corresponding tags 102a, 102b, 102c. Each tag 102a, 102b, 102c is mounted on a carafe 122 to produce a matched carafe 122a, 122b, 122c individually corresponding to a matched pair of timer 111 and signaling member 110a, 110b, 110c. A start button 112a, 112b, 112c is provided for each timer 111. Accordingly, the timer 111 that is individually actuateable by the start button 112a and labeled '1', is matched to the signaling member 110a corresponding to (e.g., it is positioned above the button 112 and may also be labeled '1'). That matched pair of timer and signaling member is in turn matched to the corresponding tag 102a that is labeled '1' on matched carafe 122a. Thus, a user may associate a signal issued by signaling member 110a with carafe 122a.

In operation a user may activate the beverage preparation device 120, by using the beverage preparation device controls 130. For example, the user may start a beverage preparation cycle to prepare a beverage to be stored in particular desired carafe 122 that is provided below dispenser 138. After the beverage preparation device 120 completes the preparation cycle (e.g., carafe 122a is full of fresh brewed coffee), the user may press start button 112a of the timer system 118 corresponding to the matched timer 111 and signaling member 110a that, in turn, correspond to the matched carafe 122a that has just had the beverage prepared by the beverage preparation device deposited into it. The start button 112a individually actuates the matched timer 111 that is included in the housing 108. The timer 111 is matched to a signaling member 110a, such that the signaling member 110 is drivingly controlled by its matched timer 111 to issue a signal after the matched timer has operated for a preset period of time. For example an LED of the matched signaling member 110a may illuminate after the matched timer 111 has operated for a preset period of time.

The preset period of time may be a default value entered on the timer. Alternatively, the user may enter the preset period of time, or alter the default preset period of time to a period of time desired by the user. Preferably, the preset period of time is correlated to the length of time the beverage prepared by the beverage preparation device 120 will stay fresh after its initial preparation. The user, therefore, can use the timer system 118 to monitor how long the beverage in the matched carafe 122 has been sitting since the beverage preparation cycle of the beverage preparation device 120 was completed.

The timer system 118 may also comprise a power source (not shown). The power source may be the power source of the beverage preparation device 120, or a wall plug, a battery, a solar panel, or a combination of any of the aforementioned sources, or any other source of power may power the power source. In some embodiments, a solar panel 114 may also be used to recharge a rechargeable battery, which in turn provides power to the power source of the timer system 118.

As mentioned previously, the signaling member 110 of the timer system 118 may issue many different signals. For example, the signaling member 110 may issue a signal indicative that the beverage in the matched carafe 122 is fresh. The signaling member 110 may display a green light for a preset period of time after the matched timer 111 is actuated, to indicate that the beverage in the matched carafe is fresh. In other examples the signaling member 110 may be any colour to indicate that the beverage is fresh. Alternatively, the signaling member may flash to indicate that the beverage is fresh, or the light may illuminate for a short period of time, and then have no indication to indicate that the beverage is fresh. Alternatively, the signaling member 110 may issue an audible sound, or an intermittent audible sound to indicate the beverage is fresh. In other embodiments, the signaling member 110 may issue both audible and visual signals to indicate the beverage in the matched carafe 122 is fresh.

After the matched timer 111 operates for a period of time following actuation by a user pressing the corresponding start button 112, the signaling member 110 may indicate that the beverage in the matched carafe 122 will only be fresh for an additional preset period of time. For example, the signaling member 110 may issue a 'warning' signal. The signaling member 110 may, for example, change from a green colour to a yellow color to indicate a warning signal about the beverage in the matched carafe 122. Alternatively, there are many possible ways that the signaling member 110 may issue a warning signal. For example, the initial indicated signal (for example a green indication) may begin to blink or flash to issue a warning signal, or the signaling member 110 may change from a state of non-indication to a state of indication (i.e. a signaling member 110 may become illuminated). In addition, for the example where the signaling member 110 blinks or flashes to issue a warning signal, the rate of flashing may progressively increase as the preset period of time for which the timer has operated decreases towards zero. As discussed above the signaling member 110 could also issue a changed or changing audio signal.

Alternately, or in addition, the signaling member 110 may also issue an end of life signal after the matched timer 111 has operated for a preset period of time, indicating that the beverage in the matched carafe 122 is no longer fresh. For example, the signaling member 110 may issue an end of life signal by indicating a red LED display. The preset period of time that the timer 111 may operate for may be a default value input into the timer 111, or a user may input the preset period of time to the timer 111. As was discussed above, the signal issued by the signaling member may be of any form, for example the use of a different colored indication light, the use of a flashing signal, or the signaling member 110 changing from an indication state to a non-indication state (i.e. the signaling member changes from illuminated to non-illuminated), or issuance of an audible signal.

In a further alternate embodiment, the signaling member may be initiated when the device 120 is initiated. Accordingly, the cycle time may include the expected time for the device to prepare the beverage. Thus, the fresh period of time may include the time required to brew the beverage.

The embodiment of FIG. 4 exemplifies a timer system 218 comprising two matched pairs of timer and signaling member 210. Elements that are similar to those in FIGS. 1-3 use the same numbers but are increased by 100.

The embodiment of timer system 218 illustrated in FIG. 4 is similar in most respects to the timer system 118 illustrated in FIG. 3, however the matched signaling members 210 are provided on the matched tags 202 instead of on the housing 208. The signaling member 210 may be drivingly controlled by the matched timer located in the housing 208 via a wired connection or a wirelessly. Any wireless technology may be used, for example Bluetooth™ technology. Thus, the signaling members 110 may be provided alone on the housing 108 or on the matched tags 202. In other embodiments, the signaling members 110, 210 may be located on both the housing 108, as well as on the matched tag 202.

The alternate embodiment of FIG. 5 further comprises a monitoring system 332. Elements that are similar to those in FIGS. 1-3 use the same numbers but are increased by 200. The monitoring system 332 is operably linked to the individual timers of the timer system 318, e.g., via a wire or via a wireless system such as, for example, Bluetooth™. Accordingly, the monitoring system 332 may record selected details of the actuations of the timer system 318 by the start buttons 312. For example, the monitoring system 332 to monitor, for example, the number of instances that the timers are actuated, the time of day of each actuation, the number of warnings or end of life signals issued, or any combination thereof. This information may be downloaded to a computer by any means known in the art and analyzed to assist the store adjust staffing or the number of carafes brewed and available at any time based on the patronage of the store.

For the embodiment of the timer system 318 illustrated in FIG. 5, each start button 312 has three signaling members, e.g., three LEDs 340, 342, 344. In this embodiment, signaling member 340, 342, 344 may indicate whether the beverage in the matched carafe is fresh, will be fresh for only an additional preset period of time (warning signal), or when the beverage is no longer fresh (end of life signal), and may need to be disposed of. This may be accomplished by, for example, illuminating the LED 340 adjacent the word 'Fresh', the LED 342 adjacent the word 'Warning' and the LED 344 adjacent the word 'Dispose' sequentially. In some examples the 'Fresh' LED 340 may be green, the 'Warning' LED 342 may be yellow and the 'Dispose' LED 344 may be red. It will be appreciated that the use of a plurality of signaling members for a specific timer may be used in any embodiment.

In monitoring the freshness of the beverage contained in the plurality of matched carafes 122, the user may dispose of the beverage in the matched carafe 122 after the signaling member 110, 210, 310 signals that the beverage in the matched carafe 122 is no longer fresh (end of life signal). This may aid the user in ensuring that the beverage being served from the plurality of carafes 122 is fresh, and therefore meets the required standard for being served to a customer.

In other embodiments, when the signaling member 110, 210, 310 issues a warning signal after the timer has operated for a preset period of time, the beverage in the matched carafe 122 may only be fresh for only an additional preset period of time. This may spur a user to attempt to serve the remainder of the beverage in the relevant matched carafe 122, while the beverage is still fresh. For example, this warning signal issued by the signaling member 110, 210, 310 may aid the user in serving the beverage in the matched carafe 122 that is closest to becoming stale. This may aid a user in less wastefully choosing which matched carafe 122, among the plurality of carafes 122, to serve a beverage from to a customer.

In addition, in the situation of a franchisee-franchisor method of organizing a business, the above-described methods of monitoring the freshness of a beverage in a plurality of carafes 122 may aid a franchisor in monitoring a franchisee's compliance with the franchisor's desired norms of serving beverages. For example, the franchisor may want the franchisee to serve only fresh beverages.

A franchisee, franchisor, or any user may also record information related to actuations of the timers of the timer system 118. This information may be recorded manually by a user, for example by the user writing down the number of actuations. Alternatively, this information may be downloaded directly from the timer system 118, at least in part by a computing device, such as a computer.

Referring to FIG. 5, in some embodiments, the computing device may be a monitoring system 332, which is operably linked via a wire or via a wireless system to the timers of the timer system 318. The computing device may be a personal computer, laptop, personal data assistant, cellular phone, centralized network computer, or any similar device. In some embodiments, the recorded information may be temporarily stored within the timer system 318 and then downloaded periodically by a user, or from time to time automatically by a computing device. The information recorded relating to actuations of the timers may relate to only a single timer, a plurality of timers, or any combination of the timers. This downloaded information permits a franchisee, franchisor, or any user to monitor the amount of usage, and/or volume of beverage produced by a given beverage preparation device 120.

Alternately, or in addition, a beverage preparation device 120 itself may also be monitored using a timer system 118, 218, 318. In one embodiment, a user may concurrently actuate a timer of the timer system 118, 218, 318 and a beverage preparation cycle of the beverage preparation device 120. For example, if the beverage preparation device 120 is a coffee brewing device, the commencement of the coffee brewing cycle is commenced concurrently with actuating the timer of the beverage freshness monitoring system timer system 118, 218, 318. The beverage preparation cycle of the beverage preparation device 120 has a predetermined cycle time. For example, the beverage preparation device 120 may have a known predetermined beverage preparation cycle time to brew a full carafe 122 of coffee. In accordance with this alternate embodiment, the signaling member 110, 210, 310 matched to the actuated timer will issue a signal after the timer has operated for a preset period of time corresponding to the predetermined beverage preparation cycle time of the beverage preparation device 120 (a "beverage preparation cycle time"). A franchisee, franchisor, or any user can therefore monitor whether their beverage preparation device 120 is operating properly. For example, if the beverage preparation device 120 takes significantly longer or shorter to prepare a beverage than its predetermined beverage preparation cycle time, the beverage preparation device 120 may be in need of servicing.

The predetermined beverage preparation cycle time may vary for different beverages, for example strong coffee may take longer to brew than weak coffee. Therefore, in some embodiments, the preset period of time that the timer of the timer system 118, 218, 318 operates before issuing a beverage preparation cycle time can be adjusted. This permits the timers of the timer system 118, 218, 318 to reflect the proper beverage preparation cycle for the beverage being prepared. It will be appreciated that the beverage preparation cycle time signal may be issued in addition to any other signal described herein.

It will be appreciated that various modifications and alterations of the embodiments noted herein may be made and each is within the scope of the following claims.

The invention claimed is:

1. A timer system for monitoring the freshness of a beverage in a plurality of carafes, the timer system comprising:
 a. a plurality of matched pairs of timers and signaling members, each timer being individually actuateable and each signaling member being drivingly controlled by its matched timer to issue a signal after the matched timer has operated for a preset period of time;
 b. a housing mountable on a beverage preparation device and including the matched pairs of timers and signaling members; and,
 c. a plurality of tags mountable on a carafe, each tag once mounted on a carafe producing a matched carafe corresponding to a matched pair of timer and signaling member.

2. The timer system of claim 1 wherein the housing is removably mountable on the beverage preparation device.

3. The timer system of claim 1 further comprising a power source.

4. The timer system of claim 3 wherein the power source comprises a battery.

5. The timer system of claim 3 wherein the power source comprises a solar panel.

6. The timer system of claim 5 wherein the power source further comprises a rechargeable battery and the solar panel is operable to recharge the rechargeable battery.

7. The timer system of claim 1 wherein the signaling member comprises at least one LED.

8. The timer system of claim 1 wherein the signaling member issues an end of life signal after the matched timer has operated for a preset period of time indicative that the beverage in the matched carafe is not fresh.

9. The timer system of claim 8 wherein the signaling member issues a warning signal after the matched timer has operated for a period of time indicative that the beverage in the matched carafe will be fresh for only an additional preset period of time.

10. The timer system of claim 9 wherein the signaling member issues a signal indicative that the beverage in the matched carafe is fresh.

11. The timer system of claim 10 wherein the signaling member comprises at least one LED.

12. The timer system of claim 1 wherein each tag includes a further matched signaling member that is wirelessly actuateable by a matched timer.

13. The timer system of claim 1 wherein the beverage is a brewed beverage.

14. The timer system of claim 1 wherein the beverage is coffee.

15. The timer system of claim 1 wherein the timer system further comprises a monitoring system that records selected details of the actuations of the timer system.

16. The timer system of claim 15 wherein the monitoring system wirelessly monitors the actuations of the timer system.

17. A timer system for monitoring the freshness of a beverage in a plurality of carafes, the timer system comprising:
 a. a plurality of matched pairs of timers and signaling members, each timer being individually actuateable and each signaling member being drivingly controlled by its matched timer to issue a signal after the matched timer has operated for a preset period of time;
 b. a housing mountable on a beverage preparation device and including the timers; and,
 c. a plurality of tags mountable on a carafe, each tag once mounted on a carafe producing a matched carafe corresponding to a matched pair of timer and signaling member;
 wherein the signaling members are provided on the tags and each signaling member is wirelessly actuateable by its matched timer.

18. A timer system for monitoring the freshness of a beverage in a plurality of carafes, the timer system comprising:
 a. a plurality of matched pairs of timers and signaling members, each timer being individually actuateable and each signaling member being drivingly controlled by its matched timer to issue a signal after the matched timer has operated for a preset period of time;
 b. a housing mountable on a beverage preparation device and including the matched pairs of timers and signaling members; and,
 c. a plurality of tags mountable on a carafe, each tag once mounted on a carafe producing a matched carafe corresponding to a matched pair of timer and signaling member wherein each tag includes a further matched signaling member that is wirelessly actuateable by a matched timer.

* * * * *